United States Patent [19]
Kamentsky

[11] Patent Number: 5,790,308
[45] Date of Patent: *Aug. 4, 1998

[54] COMPUTERIZED MICROSCOPE SPECIMEN ENCODER

[75] Inventor: Louis A. Kamentsky, Boston, Mass.

[73] Assignee: NeoPath, Inc., Redmond, Wash.

[*] Notice: The term of this patent shall not extend beyond the expiration date of Pat. No. 5,602,674.

[21] Appl. No.: 777,945

[22] Filed: Dec. 23, 1996

Related U.S. Application Data

[62] Division of Ser. No. 89,243, Jul. 9, 1993, Pat. No. 5,587,833.
[51] Int. Cl.⁶ .......................... G02B 21/26; G02B 21/34; G01J 1/20; H04N 7/18
[52] U.S. Cl. .......................... 359/393; 359/396; 359/397; 250/201.3; 250/201.8
[58] Field of Search .......................... 359/393, 396, 359/397; 250/201.3, 201.8

[56] References Cited

U.S. PATENT DOCUMENTS

| | | | |
|---|---|---|---|
| 4,769,698 | 9/1988 | Ledley et al. | 358/93 |
| 4,810,869 | 3/1989 | Yabe et al. | 250/201 |
| 5,038,035 | 8/1991 | Nishimura et al. | 250/311 |
| 5,073,851 | 12/1991 | Masterson et al. | 395/425 |
| 5,276,550 | 1/1994 | Kojima | 359/368 |
| 5,345,538 | 9/1994 | Narayannan et al. | 395/2.84 |
| 5,521,984 | 5/1996 | Denenberg et al. | 382/209 |
| 5,602,674 | 2/1997 | Weissman et al. | 359/397 |

FOREIGN PATENT DOCUMENTS 2145544  3/1985  United Kingdom ............... 359/393

Primary Examiner—Paul M. Dzierzynski
Assistant Examiner—Mohammad Y. Sikder
Attorney, Agent, or Firm—Hans L. Sun; Emil Moffa

[57] ABSTRACT

A computerized slide encoder for use with microscope analysis and pathological studies is provided. The slide encoder is attached to the movable microscope stage, whereby x-y direction plane movement and location, is correlated to examination of an identified slide, with information marking and location being directly correspondingly written, at pre-defined times, on computer storage media, during the examination. Subsequent use of the computer-stored information, coupled with the slide encoder, in a slide re-examination, permits independent retrieval of such information and location on the slide. The computer storage media includes digitized vocal transcription of history of the slide made during the original examination. An embodiment of the slide encoder includes a computer mouse pen affixed to the stage of the microscope and a rolling surface, for the mouse pen, being affixed to the movable slide holder. Examination movement of the slide causes a corresponding movement of the rolling surface and the roller ball of the mouse pen. Alternatively, the control movement of the slide holder and microscope stage is directly linked to a computer bus for a direct, software controlled, recordation of slide examination and information location markings.

16 Claims, 11 Drawing Sheets

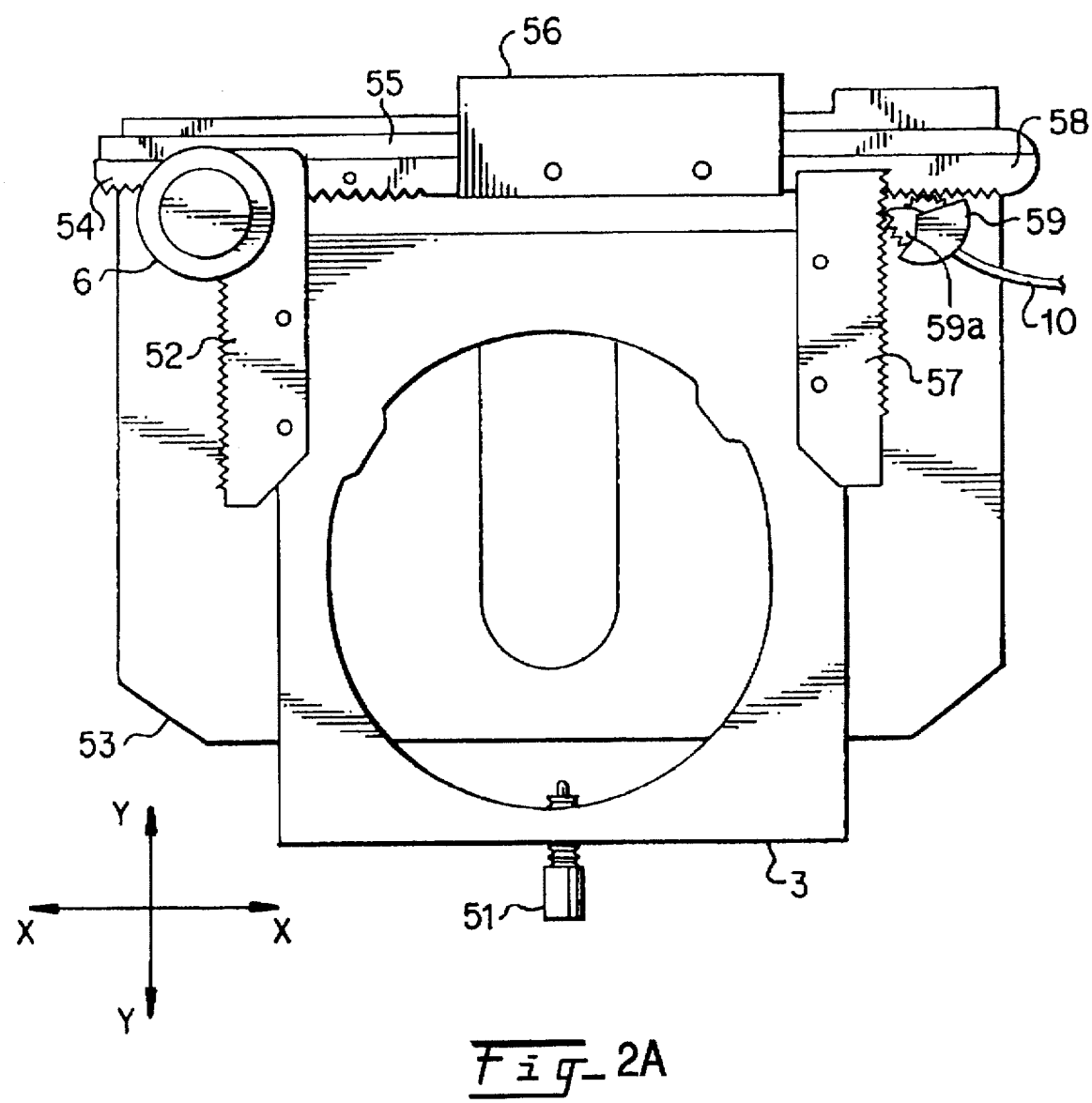
Fig_2A

COMPUTERIZED MICROSCOPE SPECIMEN ENCODER

CROSS-REFERENCE

This is a continuation of Ser. No. 08/089,243 filed Jul. 9, 1993 U.S. Pat. No. 5,587,833.

FIELD OF THE INVENTION

This invention relates to computerized location marking of information on microscope specimens such as on microscope slides, with particular utility in pathological examination and re-examination of the slides.

BACKGROUND OF THE INVENTION

Specimen slides such as Pap smears are examined by microscope users for specific types of events such as cancer cells. These events are, however, relatively rare and once found are difficult to re-locate for confirmation by others. This is a severe drawback, since an important requirement for cancer screening laboratories is certification by a pathologist, with the need for independent relocation.

The prevailing method in aiding relocation is the placement of an ink dot on the slide near the location of the event. This method has proven to be awkward, time consuming and inaccurate. In addition, with this method, it is not possible to ascertain if the entire specimen area of the slide has been uniformly examined or if the areas of the specimen have or have not been scanned. It is accordingly often the case, that if the user is interrupted, it is necessary to restart slide examination. With microscope examination of items, such as diamonds or other types of jewels, for identifying characteristics, the use of ink dots can actually detrimentally mar the appearance of the item.

Ink dot marking and other similar location methods also do not provide any information at all regarding the rate (an important quality control factor) at which each area has been examined. The dots merely function as markers and cannot provide a description of the event or any scan history record. As a result of the realization that cancer screening is inaccurate, because areas are missed, there is a major effort in place to improve the quality of screening laboratories by requiring re-screening of randomly selected slides.

In accordance with current ink dot marking practice, slides are marked with ink dots, at particular events of interest, with electrically controlled pens or marking, with the push of a button. These marking devices are exemplified by those disclosed in U.S. Pat. Nos. 3,600,057; 4,262,426; 4,690,521; and 5,076,679.

More sophisticated location methods, with event location coordinates, include those, such as disclosed in U.S. Pat. No. 4,190,314, wherein microscope slides or cover slips are marked with a grid of lines which is visible through the microscope lens. However, it is necessary to continually interrupt scanning to write down coordinates. Furthermore, no scan history is possible and special slides are required for each specimen.

Similarly, U.S. Pat. Nos. 1,996,141 and 3,514,180 provide viewable stage coordinates and modern microscopes are available with scales to determine stage position However, there is no scan history and the user must stop scanning to interpret the scale and write down the coordinates of events of interest.

Motor controlled stage or slide holder devices such as embodied in U.S. Pat. Nos. 3,999,047; 4,012,112; 4,833,382 and 5,072,382, generally provide a visible indicia on a slide for observation by the user with coordinates set into the device. The slide is moved in a meander pattern until an event of interest is discovered, at which point the slide is stopped and the position is recorded. While this provides both recording of position and a recording of scan history, it is limited by the need for the user to wait until the event comes into the field of view to stop the meander, rather than by controlling movement by hand. Such devices, besides being very expensive, also interfere with normal use of the microscope and the motion control devices thereof detract from the feel of a normal microscope stage positioning control.

Very recently, a new device has been developed which utilizes personal computers to record slide data. This device, with video input to specially modified microscopes, superimposes the display of a computer output on the microscope field for viewing by the user. A mouse is used to mark off events of interest. The device is described in *Cytometry*, vol. 13, pages 109–166 (1992) and *Analytical & Quantitative Cytology & Histology*, vol. 14, August 1992. While useful, such devices are inherently expensive and complex in requiring extensive modification of microscopes, thereby limiting their utility with respect to different field-available microscopes. As a result, widespread reviewing capability is severely restricted.

SUMMARY OF THE INVENTION

Generally, the present invention comprises an economical encoding method for microscope examination of specimens, particularly of specimen slides, and a computerized encoder device for use in such method. The method and device are suitable for encoding any microscope examined specimen which presents one or more generally planar surfaces for viewing by the microscope lens. The method and device have particular utility in the encoding of pathological slide specimens and the following discussion is with reference to such utility.

The method and device are operable with universally available personal computers or with an inexpensive modified computer device to be described hereinafter. Both method and device utilize the standard x-y plane motion of microscope slide stages and specimens such as specimen slides thereon, to effect encoding. The encoding is effected by correlating motion of the slide stage and of the slide to pixel locations on a computer generated image of the slide, for direct translation into a corresponding computer readable and storage retrievable replication. Such replication includes the motion of the slide during examination, as well as position location, on the slide, of events, and their relative degree of interest. The correlation replication and encoding is made initially with reference to preset location areas on slides to be examined. Accordingly, on review of the slide, the image and replication is retrieved by the re-initiation at such preset location area.

The encoder device of the present invention comprises, in conjunction with computer means or with integrated computer means, correlation means for translating movement of the microscope stage, with mounted slide, in the x-y plane, to retrievable corresponding computer pixel locations and cursor movement, which are stored on computer storage media linked to the computer means. The encoder device further comprises means for marking selected microscope viewing areas, as correlated to the computer pixel locations, with indicia, at pre-selected time intervals. Means are further included for marking the indicia with ratings of areas of interest and/or digitized vocalized or audio accounts. The encoder device further comprises reviewing means whereby a stored image of the indicia is reviewable, upon demand, and wherein movement of the microscope stage causes corresponding movement of a computer cursor on the image and the selected marked indicia.

With cursor location on a specific area of interest, and positioning of the specimen slide on the microscope stage, the area is directly viewable under the microscope and a voice record associated with the event can be made or retrieved.

In accordance with the present invention, the slide encoder is attached to the movable stage of essentially any microscope with a moving stage, whereby x-y plane movement and location, is correlated to examination of an identified slide, with information marking and location being directly correspondingly written on computer storage media, during or directly after the examination. The x-y plane described herein corresponds to the two dimensional viewed area of a specimen slide being examined.

Subsequent use of the computer-stored information, coupled with the slide encoder, in a slide re-examination, permits independent retrieval of such information and location on the same slide previously examined. The computer storage media may also include digitized vocal transcription of history of the slide and events, made during the original examination and/or subsequent re-examinations.

In a preferred economical embodiment of the present invention, the slide encoder includes a standard computer mouse pen affixed to the movable stage of the microscope. A stationary surface (i.e. mouse pad), for the mouse pen to roll on, may be the supporting surface for the microscope, a surface element separately affixed to the non-moving frame of the microscope stage, or any other stationary element positioned in contact with the rolling ball of the mouse. Examination movement of the slide causes a corresponding movement of the roller ball of the computer mouse pen on the rolling surface. Such movement is readily translated and stored in the computer storage media and is displayed in the form of a representative slide image on a direct viewing screen. Alternatively, the actual control movement mechanism of the slide holder is directly linked to a computer bus for a direct, software controlled, recordation of slide examination and information location markings.

In accordance with the slide encoding method of the present invention, the computer is instructed to and generates time controlled markings such as dots, which correlate to slide viewing areas, on the representative slide image. For example, at time intervals of one second, as regulated by the internal clock of the computer, a dot is generated as being representative of the full area being viewed at that time. As a result, with a subsequent review of the slide, there is a specific correlation of the computer stored dot notation via the representative slide image, directly with an actual full viewing area of the slide. It is also readily ascertainable which areas have and have not been viewed. In addition, the density of dots is a direct indication of the rate at which the slide had been examined. Thus, closely spaced dots indicate a slow scan and widely dispersed dots indicate a more rapid scan. Such information is critical for quality control evaluations.

With the marking generation or subsequent review, each marked area is readily labelled, such as with a numerical grading, to inform a reviewer of specific events and their relative importance. If desired, a digitized voice record describing the particular events being labelled may also be generated and stored for correlative retrieval upon review of the slide.

It is an object of the present invention to provide a slide encoding device for a microscope, wherein movement of the microscope stage, and slide, provides a corresponding record on computer storage media of slide examination, wherein, in effect, the microscope stage functions as a computer mouse device.

It is a further object of the present invention to provide computer generated markings, on a simulated corresponding slide image, stored on the computer storage medium, which can be retrieved and reviewed with direct relation to a review of the specific actual slide viewing, with the markings being further selectively marked for events of interest.

It is a still further object of the present invention to provide a retrievable record of events of interest, original scanning rate, specific areas scanned and a record of events of interest.

These and other objects features and advantages of the present invention will become more evident from the following discussion and drawings in which:

SHORT DESCRIPTION OF THE DRAWINGS

FIG. 1 is an isometric view of a microscope with an embodiment of the present invention in the form of a standard mouse pen affixed to the movable microscope stage;

FIG. 2A–C are bottom views of the movable microscope stage of the microscope of FIG. 1, showing direct computer connection to the movement mechanism of the microscope stage in alternative embodiments;

DETAILED DESCRIPTION OF THE INVENTION

Figure 1:
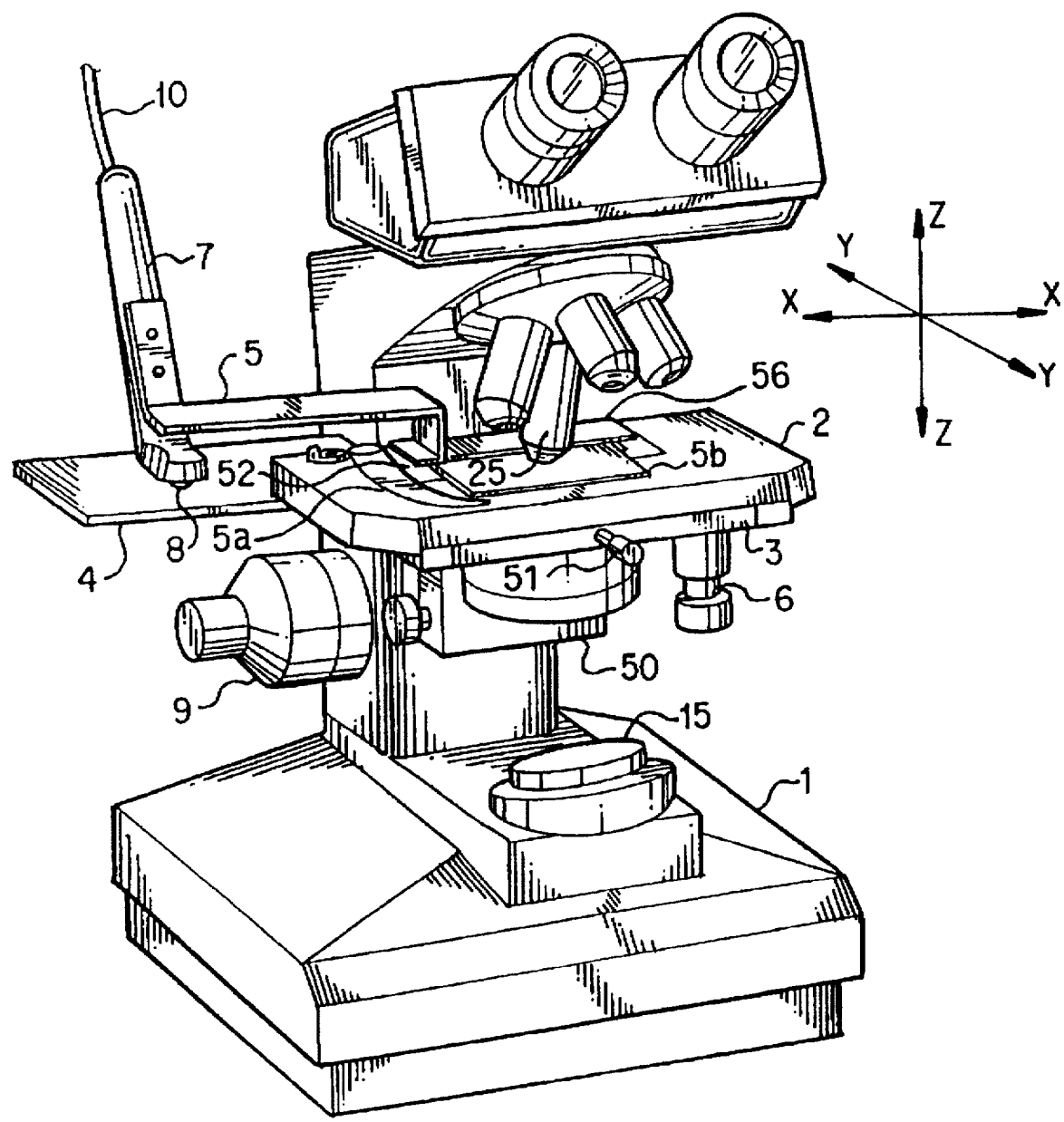

In accordance with the method of the present invention, scanning examination of a microscope slide is effected in the following manner:

1) operatively linking a computer, with a movable slide stage of a microscope, to correlatively record movement of the slide stage and a specimen such as a specimen carried on a slide, placed on the slide stage; in the x-y plane in which the slide stage and slide are movable;

2) fixedly placing an identified specimen slide on the movable stage;

3) moving the stage, with concomitant slide movement, until the microscope viewing area is fixed on a predetermined starting location point of the slide's cover slip, e.g. the upper left hand corner of the slide's cover slip;

4) initiating correlative start location by the computer, operatively linked to said movable stage, to record subsequent movement in the plane in which the stage and slide are movable;

5) moving the stage, with concomitant slide movement, away from the starting location point, with microscope examination of the slide at various locations on the slide, with the linked computer recording such motion and various locations on computer storage medium;

6) causing the computer to automatically record, on the computer storage medium, indicia (such as black dots), at pre-determined time intervals, with said indicia correlating to the microscope viewing area location on the slide, at the pre-determined time intervals; and 7) marking indicia of interest with a distinguishing marking for subsequent retrieval and recognition.

The marking of the indicia of interest is either in the form of a recognizable numerical grade indicating its relative degree of importance or the indicia is marked with a digitized voice or audio record, describing the characteristics or importance of the area being so marked. The particular indicia can be so marked at any time during slide examination or subsequent review, when the particular indica is in the microscope viewing area.

With re-examination of the slide, the slide is placed on any similarly equipped microscope slide stage (review is however independent of the type of microscope being used). At the appropriate slide viewing area start point, the recording of the particular identified slide is recovered from the computer storage medium to a viewing screen. Beginning from the reference start point correlation, a cursor on the viewing screen provides a continual correlation of position thereon to the actual microscope viewing area. Movement of the microscope stage causes concomitant movement of the cursor. As a result, the cursor can be made to fall on a selected marked indicia which correlates to the area of interest on the slide which was so marked. Such area can then be directly viewed or any audio record can be played.

The density of marked indicia on the viewing screen provides an indication of the rate at which the slide was originally examined. The denser the indicia, the slower and presumably the more careful the original examination. Absence of indicia in a particular area of the slide is indicative of such area not having been originally scanned and examined.

It is understood that the present method and device are applicable to microscope slide examination in fields other than pathological determinations, such as metal stress analysis, fingerprint analysis, etc. in which areas or events of interest are marked for subsequent review. The present method and device are also applicable to microscope examination of specimens which do not require a slide carrier, but which are fixed into position, such as with a clamp, in replicable positions. For example, identification examination and re-examination of diamonds or other gems is possible with separate x-y plane examination of the various facets for specifically located identification markings. Similarly any three dimensional object, e.g. semiconductor chips, of appropriate dimensions, can be examined and reexamined for "events of interest" in each/or any number of its surface planes.

DETAILED DESCRIPTION OF THE DRAWINGS AND THE PREFERRED EMBODIMENT

With specific reference to the drawings, in FIG. 1, a typical microscope 1 (Olympus BH-2), is shown with a slide stage 2, movable in the x-y plane shown, mounted on relatively fixed frame 3. Slide 5b, with pathological specimen to be examined, is located and fixed into position on slide stage 2, with slide holder 5a. In operation, focus control knob 9 causes frame member 3 to move in the z-direction (up and down) for focussing relative to selected lens 25. At the point of proper focus, frame 3 is fixed in position and slide stage 2 moved in the x-y direction (the two dimensional viewing area of slide 5b) for full scanning of the pathological sample on slide 5b. Concentric knob control 6 is geared, as is more clearly shown in FIG. 2, to effect such x-y direction movement.

In accordance with the embodiment of the present invention shown in FIG. 1, a first "mouse pad" element or plate bracket 4 is affixed, in a cantilevered manner to "fixed" frame 3. A standard mouse pen 7 is affixed via bracket 5 to movable slide stage 2, whereby the ball 8 of mouse pen 7 is in rolling contact with plate bracket 4. The rolling ball 8, in accordance with standard computer mouse technology is in contact, within the pen, with the surfaces of each of two cylinders with perpendicular axes. The motion of ball 8 in the x-axis direction causes one cylinder to rotate and its motion in the y-axis direction causes the other cylinder to rotate. Each cylinder is coupled with a multi-slotted disk which interrupts light between two light sources and two photo detectors and as the disks rotate, the photo detector signals are transformed by internal circuitry to the amount and directions of each of the x and y direction motions of the ball. An integrated circuit chip (e.g., Motorola PIC 16C54-XT/P) in the mouse pen 7 provides a sequence of bytes encoding this motion through connecting wire 10 to the serial bus connection on a personal computer. Standard "mouse driver" software in the computer's operating system converts these signals into the computer display screen's cursor position such as shown in FIG. 5d.

Figure 2B:
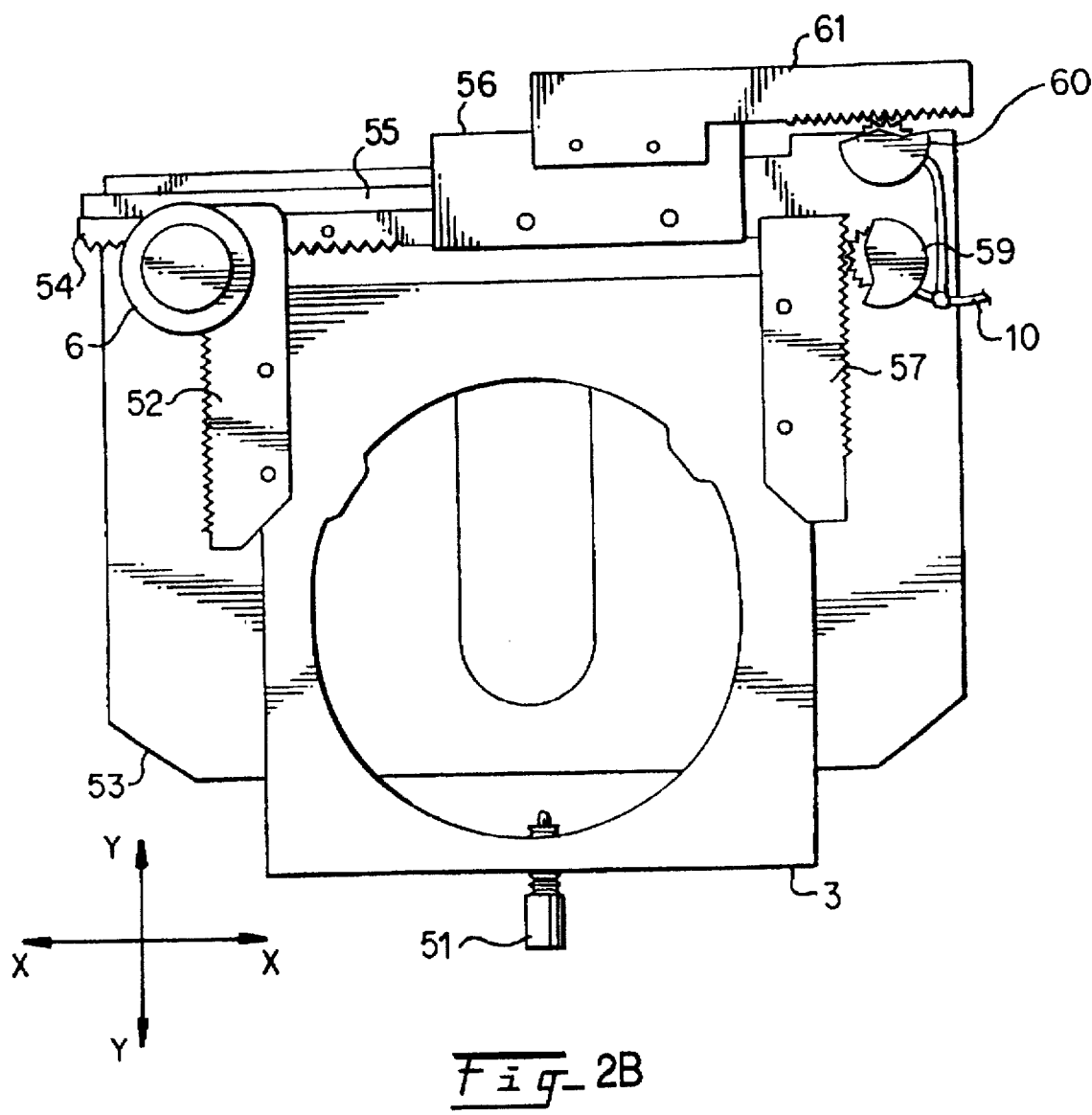

FIGS. 2A and 2B depict the geared rack movement mechanism of slide stage 2 for translation into mouse pen movement in the embodiment shown in FIG. 1. Each of the inner and outer knobs of control 6 (shown in the right hand control position) is comprised of a rotary gear (not shown), with the outer knob gear engaging geared rack 52 to cause platform 53 (and slide stage 2 thereon) to move in the y-direction relative to stage frame 3. The inner gear of control 6 (not shown) engages geared rack 54 which in turn causes bar 55, to move in the x-direction relative to platform 53, and causing attached block 56 to move in the. x-direction. Slide holder 5a, attached, in turn to block 56, is moved, thereby moving slide 5b in the x-direction.

An alternative movement and monitoring geared rack mechanism for direct, rather than the intermediate mouse monitoring movement shown in FIG. 1, is also depicted in FIG. 2A, wherein geared rack 57 is mounted on stage frame 3, whereby it causes a gear in assembly 59, mounted on platform 53 (in the left hand mount position of control 6), to rotate as the slide 5b is moved in the y-direction. A second geared rack 58 is attached to bar 55 to move the slide in the x-direction. Two concentric gears in assembly 59 cause its inner and outer shafts to rotate with the slide's x and y motion to, in turn, rotate the inner and outer shafts of a concentric shaft encoder 59a in assembly 59, such as is available from Clarostat Sensors and Controls in Plano, Tex. Each of the x and y output signals from encoder 59a is decoded into a direction signal level and incremental counts proportional to distance using a "mouse" decoder chip or a personal computer board such as is available from Technology 80, Inc. in Minneapolis, Minn. An integrated circuit decoder chip provides a sequence of bytes encoding the motion through wire 10 to a serial bus connection on a personal computer. As with the other embodiment, "mouse driver" software in the computer's operating system converts these signals into the computer display screen's cursor position. If the computer board is used, the bytes are made available directly in the computer's memory.

In a further embodiment of the present invention, shown in FIG. 2B, encoder 59a is a single shaft encoder such as is available from Dynamic Research Corporation, in Wilmington, Mass., with a gear engaging geared rack 57. In such embodiment, in place of geared rack 58, a rack 61 is mounted to block 56 so as to move with the slide's x motion. A second encoder 60, mounted to platform 53, has a geared shaft engaging geared rack 61. Encoder 60 thus encodes the x motion of the slide. The two independent encoder signals are treated as described above.

Figure 2C:
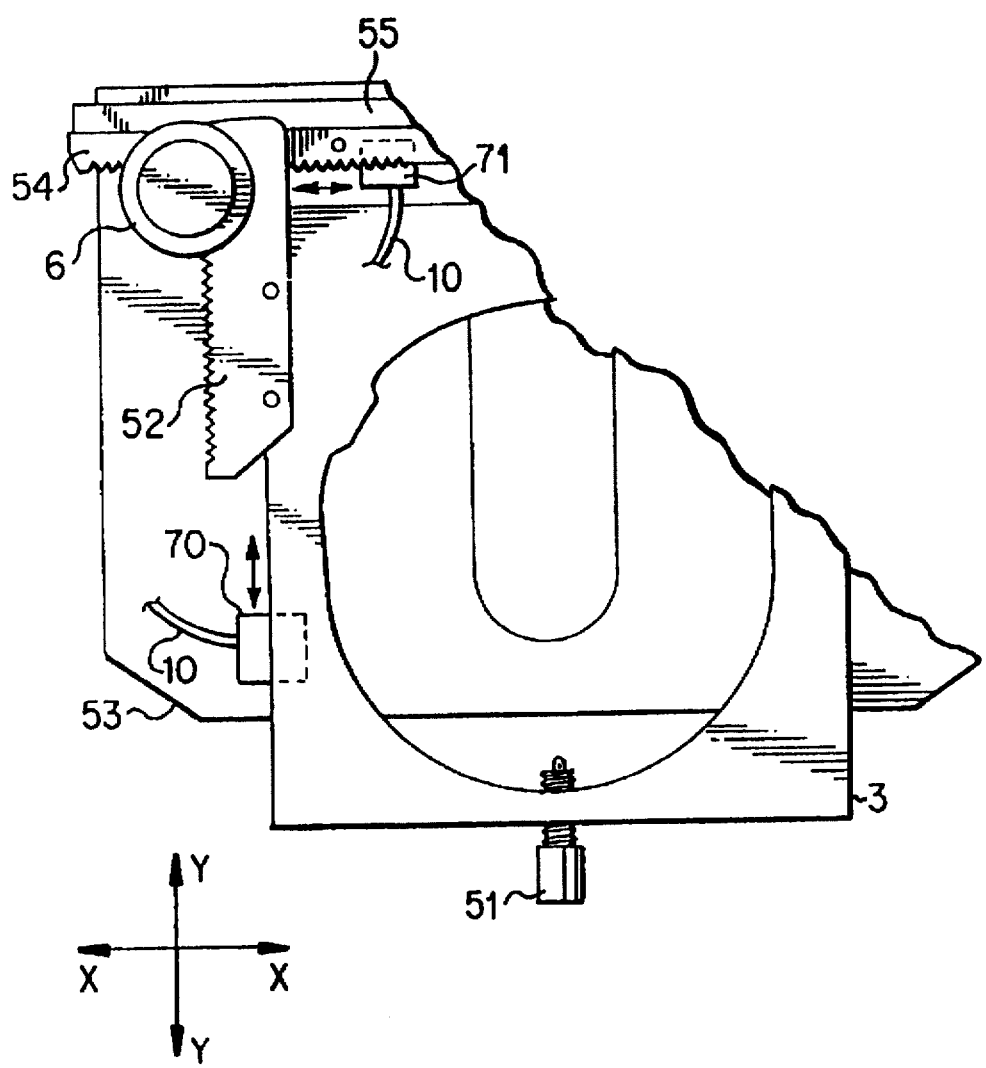

In a still further embodiment of the present invention, shown in FIG. 2C, linear encoders 70 and 71 are mounted between the frame 3 and the platform 53 and between the platform 53 and the bar 55 whereby differential motion between the slide and frame is monitored. Linear encoders of this type are available from Dynamic Research Corporation and computer boards such as from Technology 80, Inc. are used to interface them with a personal computer.

The device of the present invention can be embodied as a stage position encoding module which is plugged into one of the serial or parallel ports of a personal computer. Alternatively, in place of a standard computer with a monitor screen, the monitoring of the encoder output, via wires 10, can be effected by use of the integrated device 11 shown in FIG. 3. The device 11 integrates a personal computer board, as described above, with a small display panel 12, a special keyboard 13, an integral fixed storage device 14 such as a floppy disk or a flash card reader, and a vocal input 21. If desired, the keyboard may be a separated but connected element.

Figure 3:
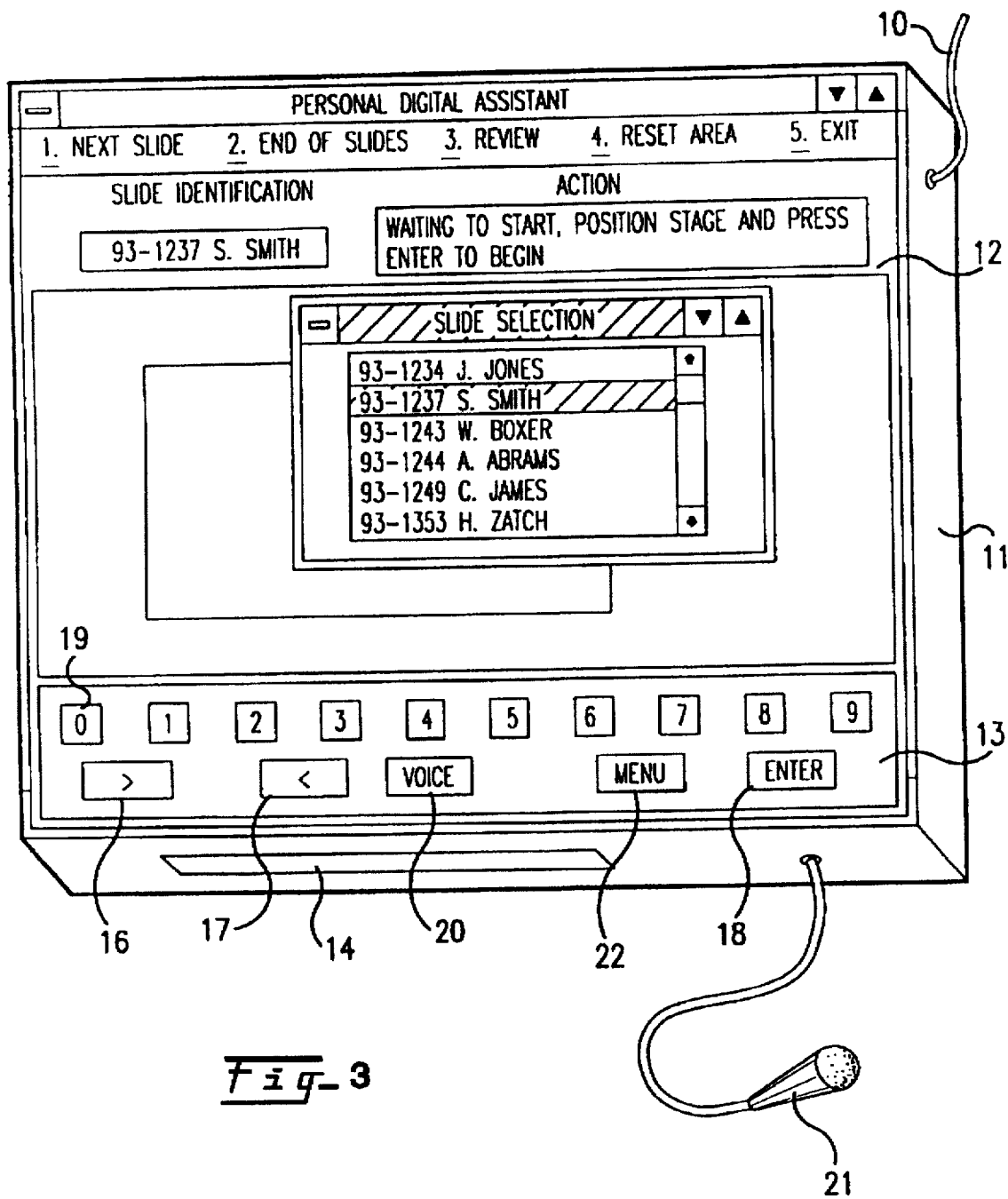
FIG. 3 is a representative view of a computer device, with viewing screen and storage capability, having marking controls, voice input and retrieval review, which is used to monitor slides with computer correlative information and to provide markings and slide scanning history.
Figure 4:
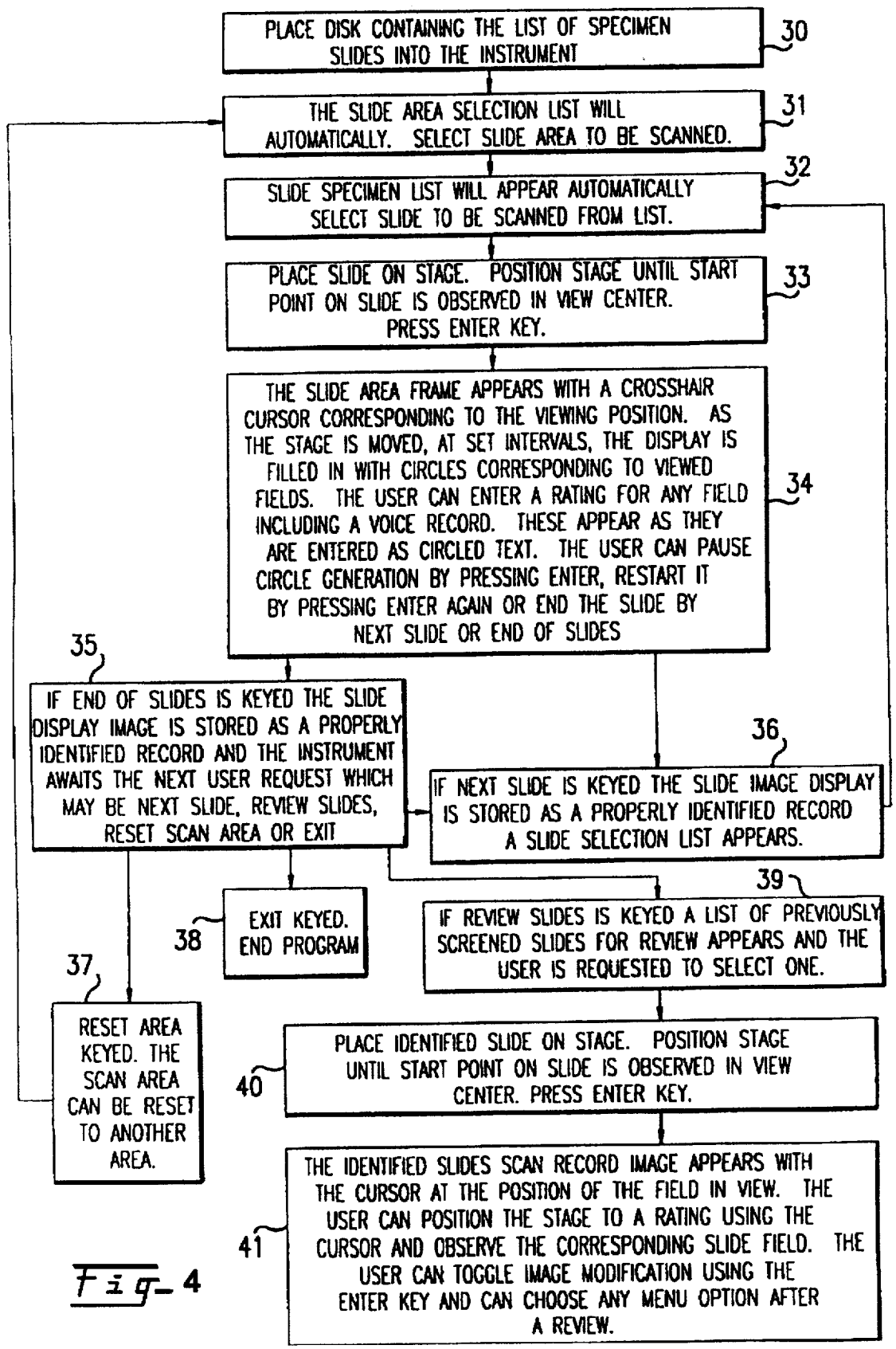
FIG. 4 is a flow chart illustrating the operative method of the present invention.
Figure 5A:
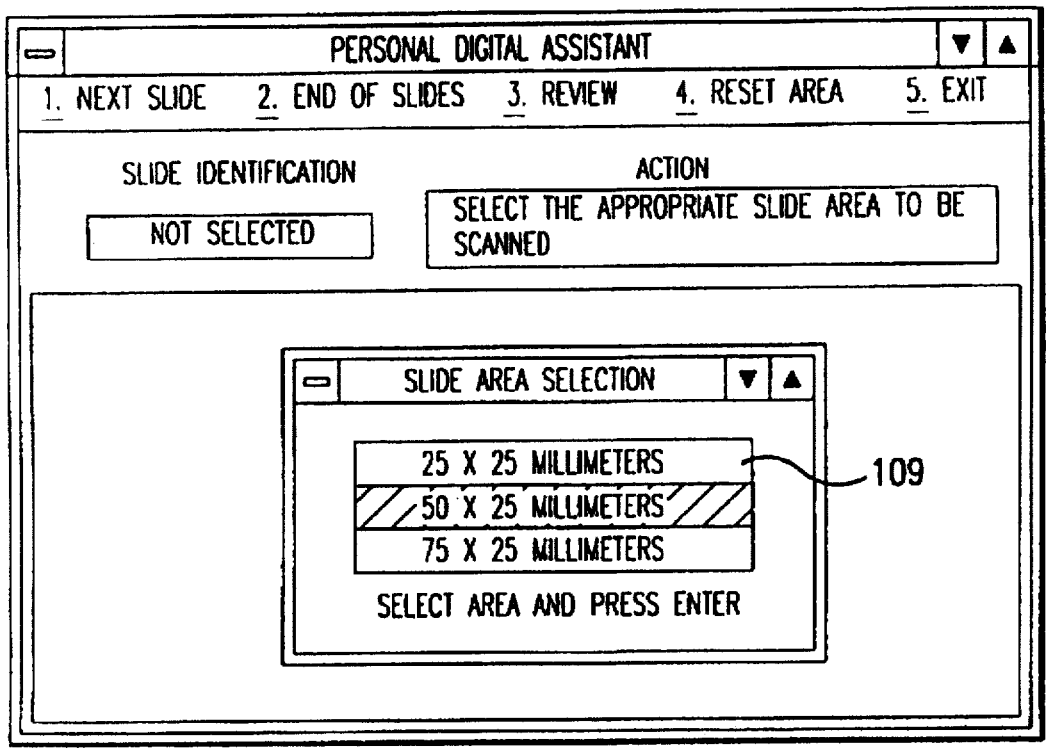
FIG. 5a is a representation of the computer view screen of FIG. 3, wherein specimen area dimensions are selected to begin the operative method as shown in FIG. 4.
Figure 5B:
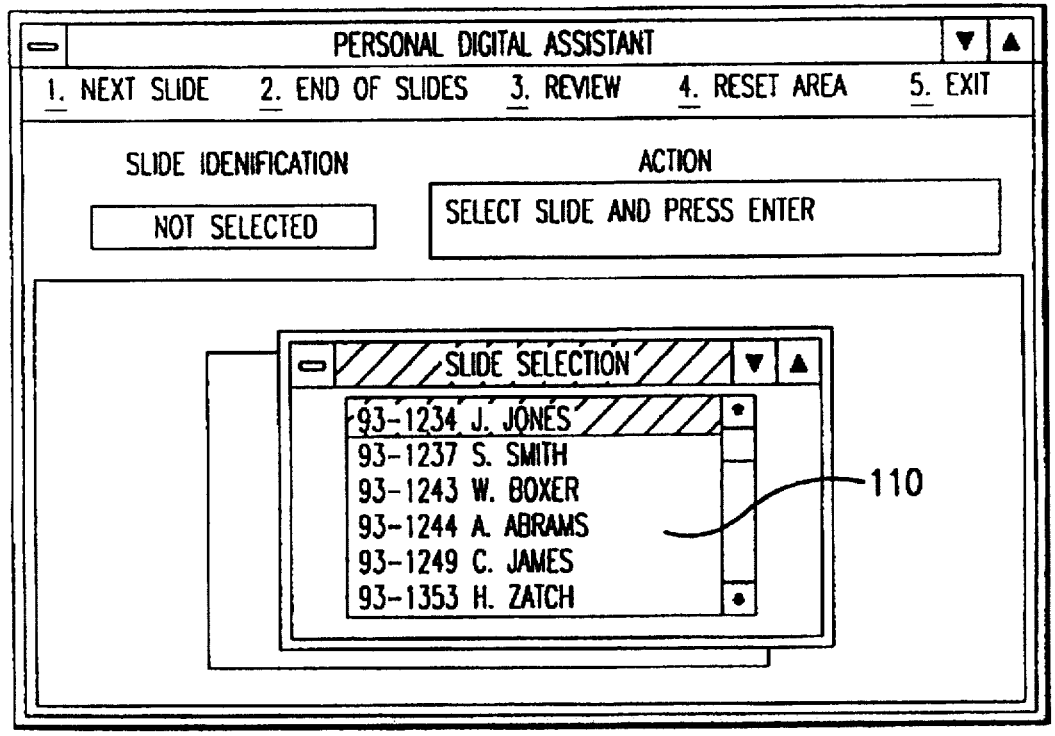
FIG. 5b is a further representation of the view screen of FIG. 3, with selection of a particular slide by name and number identification.
Figure 5C:
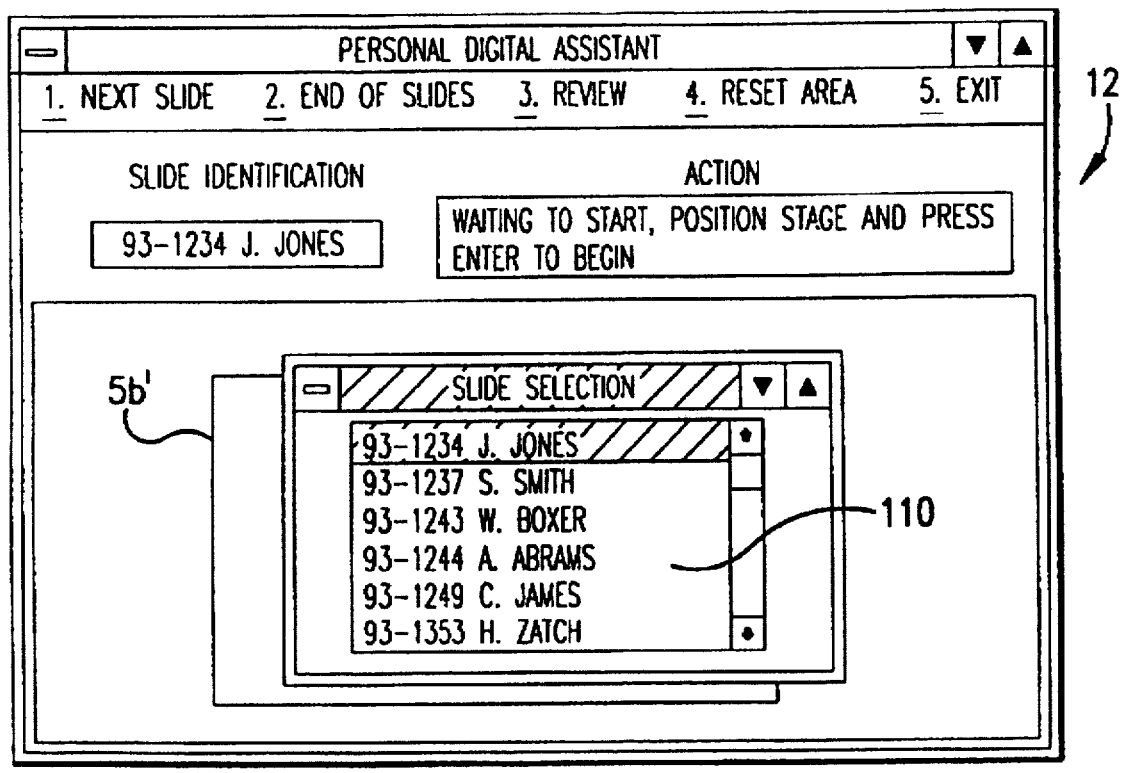
FIG. 5c is illustrative of the view screen awaiting placement of the selected slide to be examined, on the slide stage, and positioning the slide stage to the pre-determined start point.
Figure 5D:
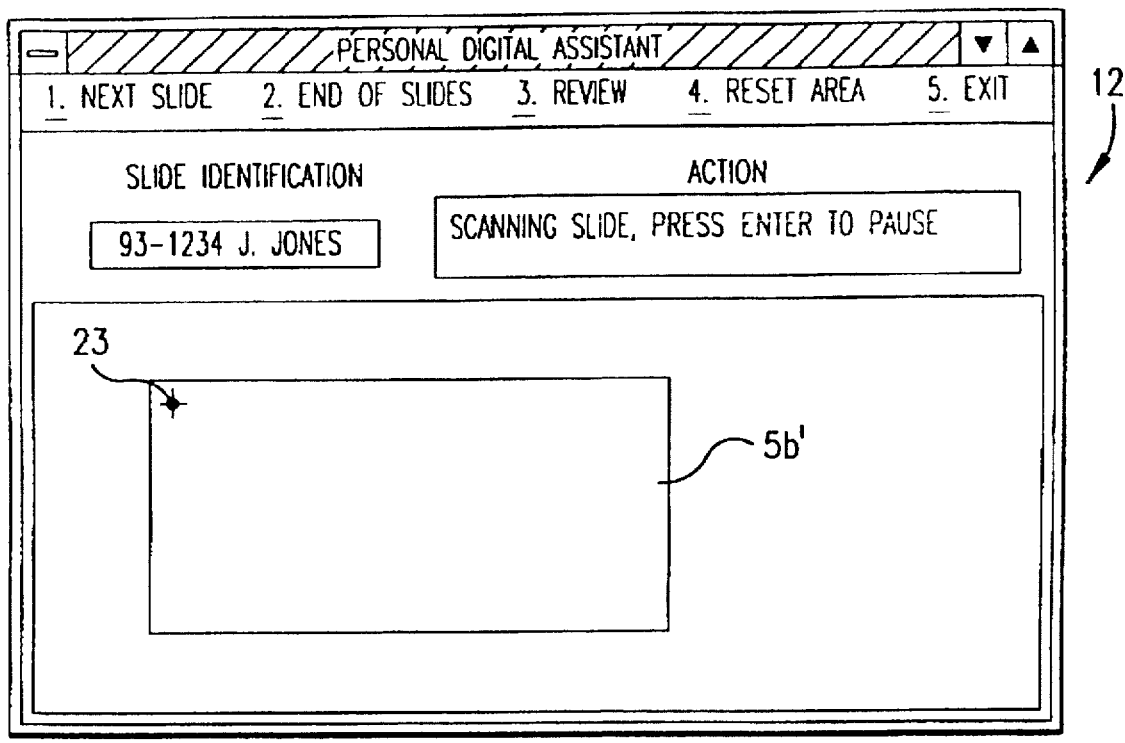
FIG. 5d is a computer generated non-magnified representation of the pathological slide selected in FIG. 5b, showing the predetermined starting point, corresponding to the actual magnified microscope viewing area, as the upper left hand corner.
Figure 5E:
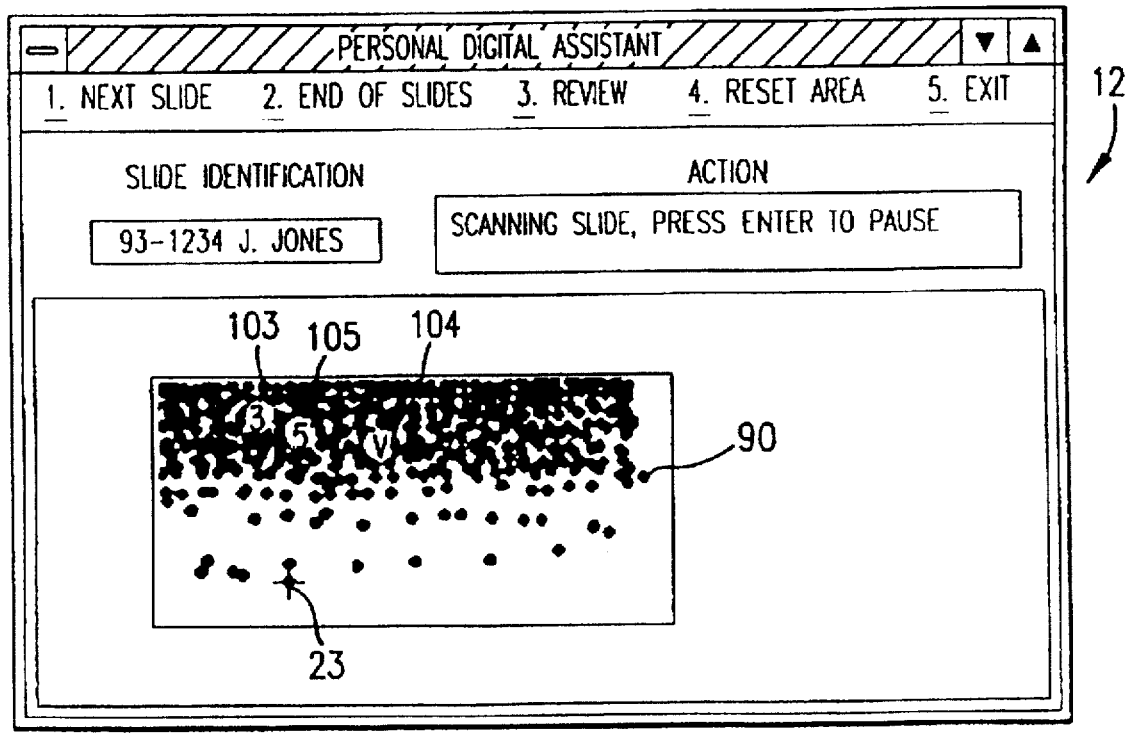
FIG. 5e shows the slide representation of FIG. 5d after slide screening, wherein dots have been generated to correspond to microscope viewing areas, with several areas having been marked as being of interest.

With reference to the flow chart of operation shown in FIG. 4, a disk with slide information (such as patient identification) is placed into the device of FIG. 3, and the screen, as shown in FIG. 5a, queries regarding the slide area to be scanned. The various menu screens are accessed by means of key 22 and appropriate selection movement is effected by use of keys 16 and 17. With selection of the desired slide area from menu list 109 (by means of entry key 18), the slide specimen list 110 (pre-entered with patient name or other identification) appears for appropriate selection as shown in FIG. 5b. With selection of the appropriate slide, the actual corresponding slide is placed on the slide stage 2, shown in FIG. 1, with the device waiting (FIG. 5c) until such placement and positioning is effected to the preselected start point on the slide cover slip by viewing through the microscope lens. As shown in FIG. 5d, a slide image 5b' appears on the screen with the crosshair cursor 23, appearing on the slide image on screen 12, at the predetermined recordation starting position (shown as the upper left hand corner of image 5b', in FIG. 5d) and scanning is initiated. As the slide stage is moved, the crosshair cursor moves correspondingly, and at pre-set time intervals, the computer enters a black dot 90 on the slide image which corresponds, in time to the microscope viewing area being scanned at the time and in area to such microscope viewing area. At any of the black dot areas 90, a numerical interest rating can be entered via the keyboard number keys 19. Alternatively, or in addition, a voice record may be made by pressing key 20 to activate microphone 21 and speaking into microphone 21. The numerical rating or voice record as well as the entered dots are recorded as a history of the slide for subsequent recall when the slide is re-examined. Thus, as shown in FIG. 5e, at the end of a scanning session, two microscope viewing areas 103 and 105 have been marked with interest levels of 3 and 5 and a vocal history was recorded and marked with a "V" at a third point 104.

Because of the density of dots, it is evident that the upper portion of the slide has been examined more intensively than the lower portion.

Figure 6A:
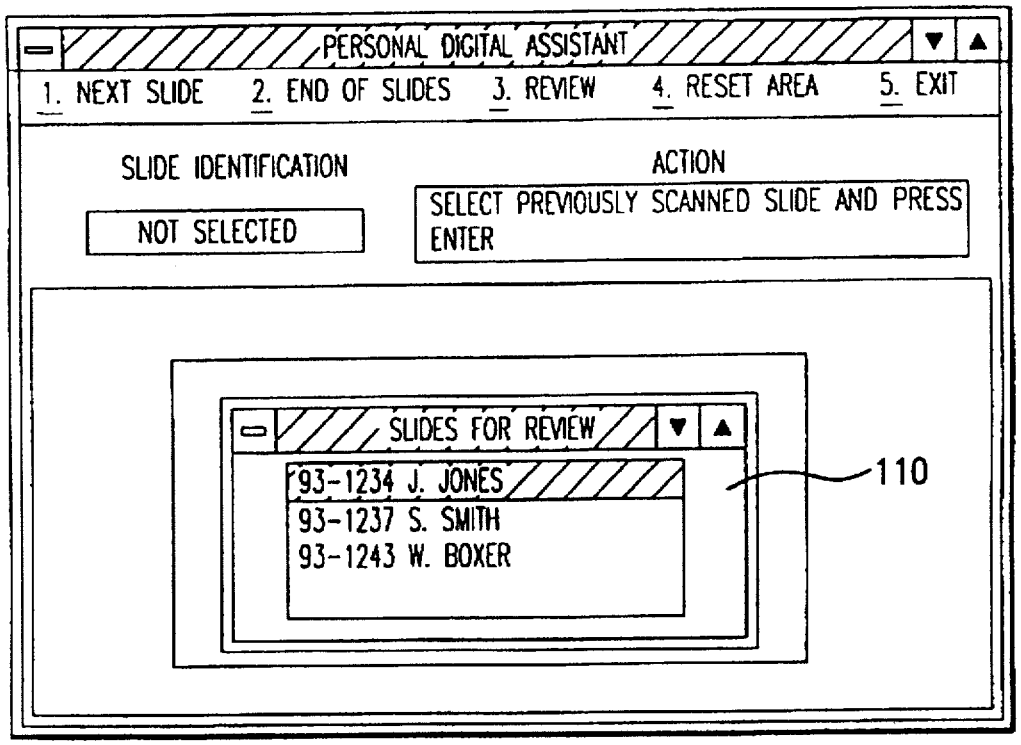
FIG. 6a represents the screen of FIG. 3 during slide information review and retrieval for slide selection.
Figure 6B:
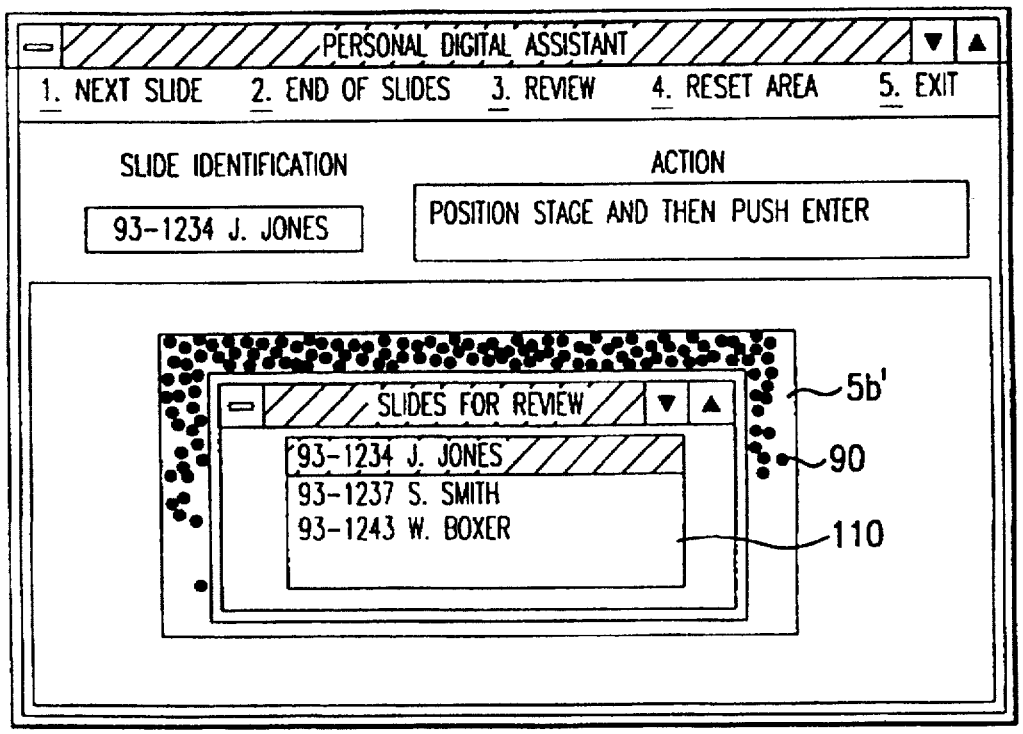
FIGS. 6b and 6c represent the screen immediately thereafter with the slide having been placed on the microscope stage and the stage being positioned at the starting point.
Figure 6C:
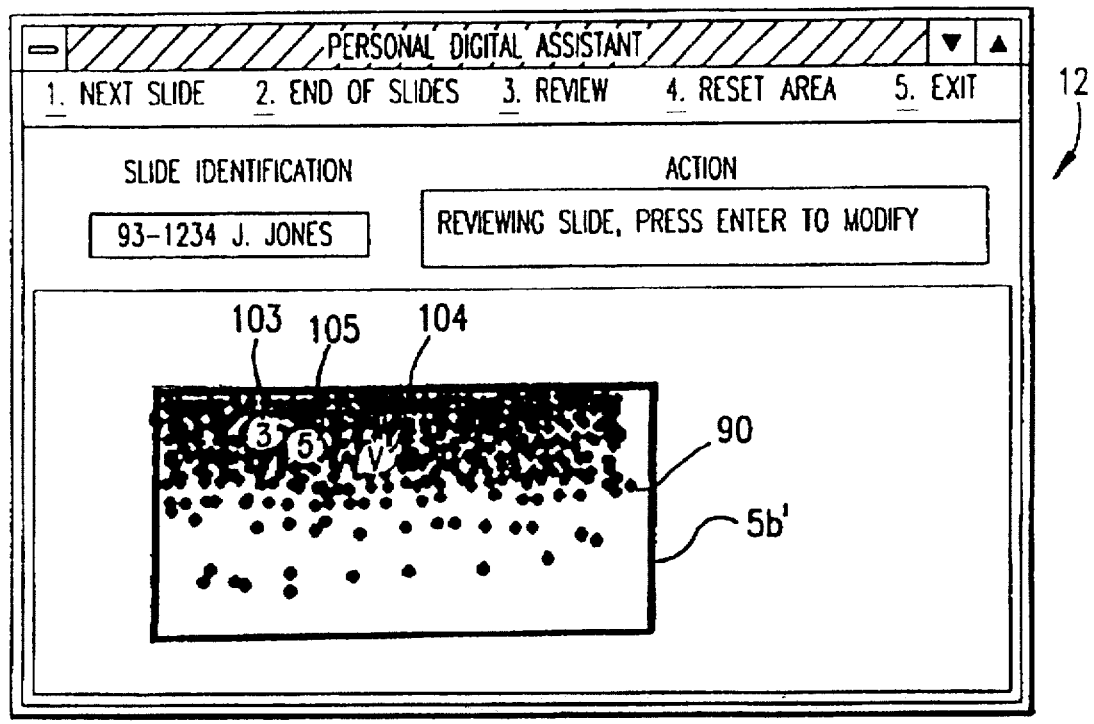
Figure 6D:
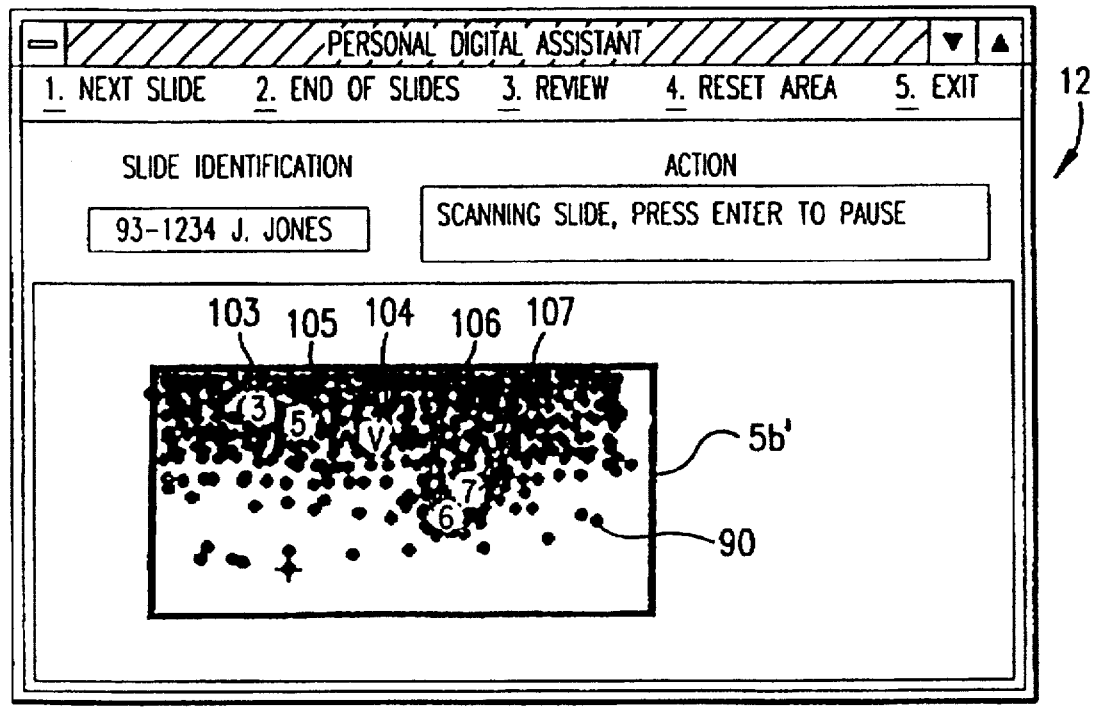
FIG. 6d represents additional areas of interest having been entered on review.

With re-examination of an already scanned slide, such as by a certifying pathologist, a slide which is identified, from menu list 110, as in FIG. 6a is recalled from computer storage. The actual slide is placed on a microscope slide stage of a similarly equipped microscope. When the stage is positioned at the predetermined starting point, review is initiated, as shown in FIGS. 6b and 6c. To view the marked points of interest (or for that matter any area), the microscope stage is moved while cursor position is monitored on the viewing screen. When the position of the cursor corresponds to that of the particular marked area of interest, it is in the viewing area of the microscope for the direct examination thereof. If a vocal history has been made, it can be replayed at such position. In addition, the slide may be re-examined during review, with additional areas being scanned or, as shown in FIG. 6d, additional areas of interest e.g. at 106 and 107 can be appropriately marked or voice records made.

It is understood that the above description, drawings and examples are merely illustrative of the present invention and that changes in procedure and components may be made without departing from the scope of the present invention as defined in the following claims.

What is claimed is:

1. A computerized specimen encoder device for use during an examination of a specimen carried on a slide mounted on a slide stage of a microscope, wherein the microscope comprises operator controlled gear elements adapted to move the slide stage in an x-y direction plane, the x-y direction plane having an x direction and a y direction, and wherein the slide stage is movable in the x-y direction plane during the examination, the computerized specimen encoder device comprising, in conjunction with computer means:

(a) a correlation means, the correlation means having a rotatable shaft encoder mounted on the microscope, for translating movement of the slide stage in the x-y direction plane, to retrievable corresponding computer pixel locations and cursor movement on a computer generated specimen image, wherein the operator controlled gear elements effect correlative motion of the correlation means;

(b) means for marking selected microscope viewing areas, as correlated to the computer pixel locations, on the computer generated specimen image, with indicia, at pre-selected time intervals; and (c) means for marking the indicia as being areas of interest for subsequent review.

2. The device of claim 1, wherein the correlation means further comprises a computer mouse element affixed to the slide stage, with the computer mouse element being positioned to operatively roll on a relatively stationary surface, in congruence with movement of the slide stage.

3. The device of claim 2, wherein the relatively stationary surface comprises a mouse pad element, affixed to a relatively stationary supporting frame for the slide stage.

4. The device of claim 1, wherein the correlation means comprises a single concentric shaft encoder having inner and outer rotatable shafts, with rotation of one of the inner and outer rotatable shafts, effected by movement of the operator controlled gear movement, correlating movement of the slide in the x direction of the x-y direction plane and rotation of an other one of the inner and outer rotatable shafts, effected by movement of the operator controlled gear movement, correlating movement of the slide in the y direction of the x-y direction plane, the device further comprising means for decoding of x and y output from the inner and outer rotatable shafts into a direction signal level and incremental counts proportional to distance.

5. The device of claim 4, wherein the means for decoding comprises a computer mouse chip.

6. The device of claim 1, wherein the correlation means comprises two rotatable shaft encoders, with rotation of a first shaft encoder, effected by movement of the operator controlled gear movement, correlating movement of the slide in the x direction of the x-y direction plane, and rotation of a second shaft encoder, effected by movement of the operator controlled gear movement, correlating movement of the slide in the y direction of the x-y direction plane, the device further comprising means for decoding of the x and y output from the first and second shaft encoders respectively into a direction signal level and incremental counts proportional to distance.

7. The device of claim 6, wherein the means for decoding comprises a computer mouse chip.

8. The device of claim 1, wherein the device further comprises the computer means and wherein the computer means comprises means for displaying the computer generated specimen image which correlates to an area of the specimen viewable by the microscope.

9. The device of claim 1, wherein the means for marking the indicia, as being areas of interest for subsequent review, effects the marking by assigning a numerical grading to selected indicia.

10. The device of claim 1, wherein the means for marking the indicia, as being areas of interest for subsequent review, effects the marking by providing a digitized audio record, with information relating to the selected indicia.

11. A computerized specimen encoder device for use during an examination of a specimen on a slide mounted on a slide stage of a microscope, wherein the microscope has a member fixed in position relative to movement of the slide stage in an x-y direction plane, and wherein the slide stage is movable in thee x-y direction plane during the examination; the computerized specimen encoder device comprising, in conjunction with computer means:

(a) correlation means for translating movement of the slide stage with mounted specimen, in the x-y direction plane, to retrievable corresponding computer pixel locations and cursor movement on a computer generated specimen image, the correlation means further comprising first and second linear encoder elements, with the first of the linear encoder elements being mounted between the fixed member and the slide stage, to monitor relative movement there between in one of the x and y directions in the x-y direction plane and with the second of the linear encoder elements being mounted between the slide stage and the slide, to monitor relative movement there between in the other of the x and y directions;

(b) means for marking selected microscope viewing areas, as correlated to the computer pixel locations, on the computer generated specimen image, with indicia, at pre-selected time intervals; and (c) means for marking the indicia as being areas of interest for subsequent review.

12. The device of claim 11, wherein the correlation means further comprises a computer mouse element affixed to the slide stage, with the computer mouse element being positioned to operatively roll on a relatively stationary surface, in congruence with movement of the slide stage.

13. The device of claim 12, wherein the relatively stationary surface comprises a mouse pad element, affixed to a relatively stationary supporting frame for the slide stage.

14. The device of claim 11, wherein the device further comprises the computer means and wherein the computer means comprises means for displaying the computer generated specimen image which correlates to an area of the specimen viewable by the microscope.

15. The device of claim 11, wherein the means for marking the indicia, as being areas of interest for subsequent review, effects the marking by assigning a numerical grading to selected indicia.

16. The device of claim 11, wherein the means for marking the indicia, as being areas of interest for subsequent review, effects the marking by providing a digitized audio record, with information relating to the selected indicia.

* * * * *